(12) United States Patent
Hofmann et al.

(10) Patent No.: US 11,419,568 B2
(45) Date of Patent: Aug. 23, 2022

(54) MULTI-ENERGY METAL ARTIFACT REDUCTION

(71) Applicant: Siemens Healthcare GmbH, Erlangen (DE)

(72) Inventors: Christian Hofmann, Erlangen (DE); Bernhard Schmidt, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 522 days.

(21) Appl. No.: 16/432,018

(22) Filed: Jun. 5, 2019

(65) Prior Publication Data

US 2019/0380670 A1    Dec. 19, 2019

(30) Foreign Application Priority Data

Jun. 13, 2018  (EP) ..................................... 18177518
Mar. 18, 2019 (EP) ..................................... 19163423

(51) Int. Cl.
*A61B 6/00* (2006.01)
*A61B 6/03* (2006.01)
*G06T 11/00* (2006.01)
*G16H 30/40* (2018.01)
*G06T 7/00* (2017.01)

(52) U.S. Cl.
CPC .......... *A61B 6/5258* (2013.01); *A61B 6/032* (2013.01); *A61B 6/482* (2013.01); *G06T 11/008* (2013.01); *G06T 7/0012* (2013.01); *G06T 2207/10081* (2013.01); *G06T 2211/408* (2013.01); *G16H 30/40* (2018.01)

(58) Field of Classification Search
None
See application file for complete search history.

(56) References Cited

U.S. PATENT DOCUMENTS

| 2011/0081071 | A1 | 4/2011 | Benson et al. |
| 2015/0078507 | A1* | 3/2015 | Kyriakou ............. A61B 6/4085 378/4 |
| 2016/0324499 | A1* | 11/2016 | Sen Sharma .......... A61B 6/032 |

FOREIGN PATENT DOCUMENTS

WO    WO-2015168147 A1 *  11/2015    ........... G06T 11/008

OTHER PUBLICATIONS

Meyer, Ester et al.: "Normalized Metal Artifact Reduction (NMAR) in Computed Tomography", in: Med. Phys. 37, vol. 10, Oct. 2010, pp. 5482-5493, DOI:10.1118/1.3484090; 2010.
(Continued)

*Primary Examiner* — Vu Le
*Assistant Examiner* — Courtney Joan Nelson
(74) *Attorney, Agent, or Firm* — Harness, Dickey & Pierce, P.L.C.

(57) ABSTRACT

A method is for metal artifact reduction in CT image data, the CT image data including multiple 2D projection images acquired using different projection geometries and suitable to reconstruct a 3D image data set of a volume of an imaged object. In an embodiment, the method includes a metal artifact reduction process including at least, acquiring, using a multi-energy CT technique, energy-resolved CT image data associated with multiple energy ranges. At least one result of the multi-energy technique is used in at least one aspect of the metal artifact reduction process.

17 Claims, 4 Drawing Sheets

(56) References Cited

OTHER PUBLICATIONS

Yu, Hengyong et al. "A Segmentation-Based Method for Metal Artifact Reduction" Technical Report, Academic Radiology, vol. 14, No. 4, pp. 495-504, Apr. 2007 // DOI: https://doi.org/10.1016/j.acra.2006.12.015.

Bin Radin Nasirudin, Radin Adi Aizudin "Analysis of multi-energy spectral CT for advanced clinical, pre-clinical, and industrial applications" Dissertation; TU Munich; Fakultät für Medizin, 2015 // http://medlatum.ub.tum.de?id=1233516.

Extended European Search Report dated Oct. 4, 2019.

\* cited by examiner

MULTI-ENERGY METAL ARTIFACT REDUCTION

PRIORITY STATEMENT

The present application hereby claims priority under 35 U.S.C. § 119 to European patent application numbers EP 18177518.0 filed Jun. 13, 2018, and EP 19163423.7 filed Mar. 18, 2019, the entire contents of each of which are hereby incorporated herein by reference.

FIELD

Embodiments of the invention generally relate to a method and system for metal artifact reduction in computed tomography (CT) image data. Embodiments of the invention further generally relate to a computer program, which performs the steps of the inventive method, if the computer program is executed on a computer, and to an electronically readable storage medium, on which such a computer program is stored.

BACKGROUND

Methods for reconstructing tomographic image datasets from projection image data from a scan of an object by a CT system are generally known. If metal items are located in the object, strong image artifacts, known as metal artifacts, which appreciably reduce the quality of the reconstructed image, arise on account of increased beam hardening, more scattered radiation, a partial volume effect and increased noise.

CT images with metal artifacts are corrupted by artifacts which can be separated into low frequency artifacts (mainly generated by beam hardening processes) and into high frequency (HF) artifacts (mainly generated due to noise increase due to photon starvation and the fact that the limited spatial resolution in the presence of very "sharp" high attenuation structures generates inconsistencies/streaks during reconstruction).

Current approaches established in the literature and implemented by different vendors are based on the mechanism called "normalized sinogram interpolation" (see, for example, the article in Med Phys. 2010 October; 37(10): 5482-93; "Normalized metal artifact reduction (NMAR) in computed tomography" by Meyer E, Raupach R, Lell M, Schmidt B, Kachelriess M.) to replace the parts of the sinogram which are corrupted by the metal trace.

SUMMARY

The inventors have discovered that the above-noted methods are prone to errors in particular in cases in which the metal artifacts are mistaken for metal objects themselves during thresholding or in which other highly attenuating materials are present, such that suboptimal results are achieved.

At least one embodiment of the current invention provides a device/method for improving the performance of metal artifact reduction algorithms for CT image data, in particular yielding increased image quality.

Embodiments of the invention are directed to a method, a system, a computer program and an electronically readable storage medium. Advantageous embodiments are described by the claims.

In at least one embodiment, a metal artifact reduction process comprises:

segmenting metal areas in the projection domain and/or the image domain, correcting the projection images by replacing projection image data by interpolated data in the metal areas, and reconstructing an artifact-reduced 3D image data set from the so-corrected projection images.

An embodiment of the invention further concerns a system for metal artifact reduction in CT image data, comprising at least one central processing unit or a computer for the evaluation of image data, wherein a method according to an embodiment of the invention is implemented on the central processing unit or the computer of the system. All remarks and comments regarding the method also apply to the system.

Preferably, the system is or comprises a medical imaging system. An embodiment of the invention may thus also relate to a medical imaging system, such as a computed tomography system, which includes a central processing unit or a computer for the evaluation of image data, wherein a method according to an embodiment of the invention is implemented on the central processing unit or the computer of the medical imaging system. In this manner, all postprocessing, that is, in particular, the whole reconstruction pipeline, may be realized in the computed tomography apparatus where the projection images have been acquired.

According to another embodiment of the present invention, it is provided that components of the system are part of a network, wherein preferably the network and a medical imaging system which provides the image data are in communication with each other. Such a networked solution could be implemented via an internet platform and/or in a cloud-based computing system. In other words, the central processing unit or the computer may be part of a network communicating with the medical imaging system.

An embodiment of the invention further provides a computer-readable medium on which are stored program elements that can be read and executed by a computer in order to perform steps of a method according to an embodiment of the invention and its various embodiments when the program elements are executed by the computer.

An embodiment of the invention further provides a computer program product with program elements that can be read and executed by a computer in order to perform steps of a method according to an embodiment of the invention and its various embodiments when the program elements are executed by the computer.

Further there is provided an electronically readable storage medium, on which a computer program as described above is stored.

BRIEF DESCRIPTION OF THE DRAWINGS

Further details and advantages of the current invention can be taken from the following description of detailed embodiments taken in conjunction with the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to at least one embodiment of the invention, multi-energy information is used to improve metal artifact reduction, segmentation or imaging tasks. CT systems with the ability to resolve different x-ray photon energies provide CT image data in a plurality of data sets or projection image data sets which relate to the same object. Image data sets of this type are recorded, for example, using a plurality of energy thresholds, resulting in multi-energy scans. In such multi-energy scans, data of a photon-counting detector is provided with one or more energy thresholds, wherein different data subsets are assigned to the respective energy ranges separated by the energy thresholds. In other words, preferably, the multi-energy CT image data is acquired in a single scan by using a photon counting detector using at least one energy threshold.

Alternatively, data sets of projection image data relating to different energy ranges or energy spectra can be obtained by scanning the object separately with x-rays of different respective energy ranges or energy spectra. This is, however, less preferred, since, with photon counting, CT multi-energy imaging information can be used in every scan and thus algorithmic steps in current CT reconstruction pipelines can make use of the multi-energy information to improve for example the result of metal artifact reduction algorithms as described in this document. In other words, additional multi-energy information can be obtained without noteworthy effort.

These energy resolved image data sets come with the advantage of additional spectral information. This means that multi-energy based applications can be incorporated in the reconstruction pipeline and can be used as additional input for other algorithmic steps like the metal artifact reduction. The following multi-energy based applications can be used to improve algorithmic steps in metal artifact reduction such as e.g. "normalized sinogram interpolation" based metal artifact reduction approaches:

1. Use of optimal energy threshold for a segmentation or imaging task.

2. Use of highest threshold (i.e. highest bin image→hardest spectrum) for metal segmentation, and bone mask generation (highest bin has least metal artifacts due to beam hardening and thus is best suited for thresholding).

3. Use spectral information for different algorithmic steps, e.g. masks, segmentation, or material classification to generate material specific thresholding masks (e.g. distinguish bone and iodine and treat them differently during thresholding). A multi-energy evaluation can be used for the different thresholding tasks.

As known, when working with the 2D projection images or other information in projection space, this may be termed working in the projection domain, as opposed to the 3D image space, the image domain.

According to one embodiment of a method, in a first step, metal can be segmented in the image domain by thresholding, e.g. based on the use of the highest threshold or highest bin. An (e.g. 3D) forward projection can identify the metal trace in the original projections. Before interpolation, the projections can be normalized based on a (3D) forward projection of a prior image. This prior image can be obtained, for example, by a multithreshold segmentation of the initial image, e.g. by using the highest threshold. The original raw data can be divided by the projection image data of the prior image and, after interpolation, be denormalized again. Simulations and measurements can be performed to compare normalized metal artifact reduction (NMAR) to standard metal artifact reduction (MAR) with linear interpolation and MAR based on simple length normalization.

In at least one embodiment, a metal artifact reduction process comprises:

segmenting metal areas in the projection domain and/or the image domain, correcting the projection images by replacing projection image data by interpolated data in the metal areas, and reconstructing an artifact-reduced 3D image data set from the so-corrected projection images.

In concrete embodiments, the segmentation is performed in the image domain by thresholding, wherein the metal areas in the projection images are determined by forward projection and interpolation is performed in the projection domain. Any known MAR technique from the state of the art may be employed here, in particular regarding the interpolation step, such that these options will not be discussed here in detail.

However, as can be shown and was surprisingly discovered during the current invention, the highest energy range data subset of the energy-resolved CT image data, i.e. the "highest bin" or "highest threshold", substantially less metal artifacts are encountered. Thus, in a first concrete advantageous embodiment, CT image data associated with the highest energy range, in particular determined using the highest threshold in a photon counting detector, is used for the metal segmentation step, in particular in the image domain.

If, thus, an initial reconstruction is performed using only the projection image data of the highest energy range, this initial reconstruction will have less metal artifacts, simplifying the tasks of segmentation substantially, such that improved segmentation results are achieved in the image domain. Of course, if further segmentation of other high attenuation materials, for example bone, is performed in the imaging pipeline, in particular during the metal artifact reduction process, the highest energy range data can, of course, also be advantageously used instead of the full CT image data/projection image data. For example, a high attenuation material mask, in particular a bone mask, may be determined based on the highest energy range data.

In embodiments of the invention, NMAR as discussed above, in particular normalized sinogram interpolation, may also be used as the metal artifact reduction process. That is, preferably, before the interpolation step, the projection images are normalized based on a forward projection of a 3D prior image determined from a 3D initial image, which is reconstructed from the originally acquired projection images, by multi-threshold segmentation, wherein the projection images are denormalized after interpolation. For example, the prior image may distinguish between water-like tissue and bone-like tissue; however, further materials and/or attenuation value ranges may be used. In the normalization process, the result of the multi-energy technique may also be advantageously used.

Preferably, in a first embodiment, the 3D initial image is reconstructed from CT image data associated with the highest energy range, in particular determined using the highest threshold in a photon counting detector, as already explained above. Due to the fact that such an initial image has less artifacts, a higher quality segmentation to determine the 3D prior image is possible.

In another advantageous embodiment, spectral information determined as a result of the multi-energy technique may be used for refining the multi-threshold segmentation and/or for material classification when determining the prior image. For example, if the imaged volume comprises bone as well as iodine or other combinations of high attenuation materials, the energy-resolved CT image data may be analysed to distinguish between such materials which would not be distinguishable otherwise. For example, a multiple-materials decomposition may be performed in areas having the same general attenuation values. Such material decompositions in multi energy CT are known from the state of the art.

But also generally, it is advantageous to use spectral information determined as a result of the multi-energy technique for segmentation and/or material classification steps, for example for the definition of material specific thresholding masks. In particular, if the spectral information is used to distinguish between metal and iodine, the interpolation may be restricted to metal areas, excluding iodine areas, and the like. In this manner, important image information is conserved.

As already discussed, it is preferred to acquire the multi-energy CT image data in a single scan by using a photon counting detector using at least one energy threshold. In such a case, in advantageous embodiments, at least one energy threshold is chosen depending on at least one use of the result of the multi-energy technique in the at least one step of the metal artifact reduction process and/or depending on at least one imaging task information. If, for example, the highest energy range data are to be used to better segment metal and/or other high attenuation materials, the threshold may be chosen allow as few artifacts as possible, yet yielding enough highest energy range data in the subset to allow for the segmentation.

In another example, if it is known that the image volume will contain iodine, metal and bone, energy thresholds may be chosen to allow optimal decomposition of these materials. In general, if the imaging task information describes at least two materials in the volume to be imaged having comparable attenuation values in reconstructed 3D images, the energy thresholds may be chosen to allow optimal decomposition of these materials. Of course, the imaging task information may also describe other properties in the volume to be imaged and/or the general objective of the acquisition. For example, thresholds may be adjusted to the region of interest of a body of a patient.

An embodiment of the invention further concerns a system for metal artifact reduction in CT image data, comprising at least one central processing unit or a computer for the evaluation of image data, wherein a method according to an embodiment of the invention is implemented on the central processing unit or the computer of the system. All remarks and comments regarding the method also apply to the system.

Preferably, the system is or comprises a medical imaging system. An embodiment of the invention may thus also relate to a medical imaging system, such as a computed tomography system, which includes a central processing unit or a computer for the evaluation of image data, wherein a method according to an embodiment of the invention is implemented on the central processing unit or the computer of the medical imaging system. In this manner, all postprocessing, that is, in particular, the whole reconstruction pipeline, may be realized in the computed tomography apparatus where the projection images have been acquired.

According to another embodiment of the present invention, it is provided that components of the system are part of a network, wherein preferably the network and a medical imaging system which provides the image data are in communication with each other. Such a networked solution could be implemented via an internet platform and/or in a cloud-based computing system. In other words, the central processing unit or the computer may be part of a network communicating with the medical imaging system.

An embodiment of the invention further provides a computer-readable medium on which are stored program elements that can be read and executed by a computer in order to perform steps of a method according to an embodiment of the invention and its various embodiments when the program elements are executed by the computer.

An embodiment of the invention further provides a computer program product with program elements that can be read and executed by a computer in order to perform steps of a method according to an embodiment of the invention and its various embodiments when the program elements are executed by the computer.

Further there is provided an electronically readable storage medium, on which a computer program as described above is stored.

In the following, embodiments for improving metal artifact reduction (MAR) in CT image data of an imaging volume of a patient are described. These embodiments exploit the fact that a computed tomography apparatus having a photon counting detector is used, which can thus be controlled to acquire energy resolved CT image data according to energy thresholds defining at least two energy ranges. Single photon events are counted according to the energy of the photons.

Figure 1:
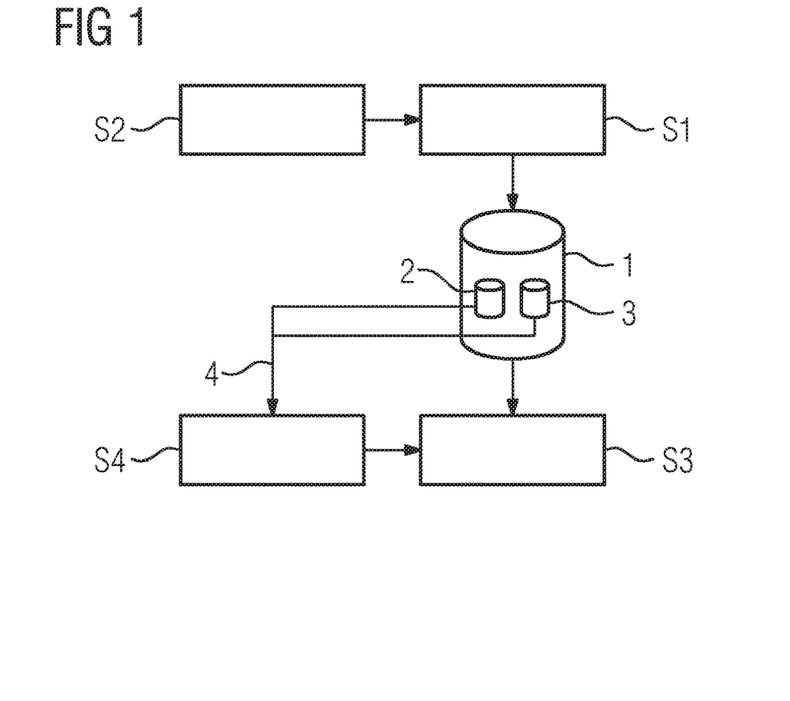
FIG. 1 shows a general flow chart for embodiments of the method according to the invention.

FIG. 1 shows a general overview. In a step S1, 2D projection images are acquired using different projection geometries, for example different projection angles along a circular acquisition trajectory. For this imaging process, in a step S2, energy thresholds for the photon counting detector are determined which are best suited for the postprocessing/reconstruction pipeline. For example, if it is known that the imaging volume comprises metal, iodine and bone, the energy thresholds and thus energy ranges may be chosen such that a material decomposition for those materials has the best separation performance. In other cases or additionally, at least the highest energy threshold may be chosen such that as few as possible artifacts are present in a 3D reconstruction using solely the highest energy range data, while still providing enough image quality such that a reliable segmentation, in particular of metal areas, may be performed.

The resulting CT image data 1 is thus comprised of subsets 2, 3 containing energy range data for respective energy ranges. While, in this example, for reasons of simplicity only two energy ranges and thus two subsets 2, 3 are shown, there may, of course, be further energy thresholds and thus energy ranges defined and used.

In a step S3, the reconstruction of a 3D image data set from the 2D projection images of the CT image data 1 is performed. As a part of this reconstruction pipeline, a metal artifact reduction process is executed in step S4. At least one step of this metal artifact reduction process uses the result of the multi-energy technique employed to improve the artifact reduction, as indicated by joined arrow 4 emanating from the subsets 2, 3.

Figure 2:
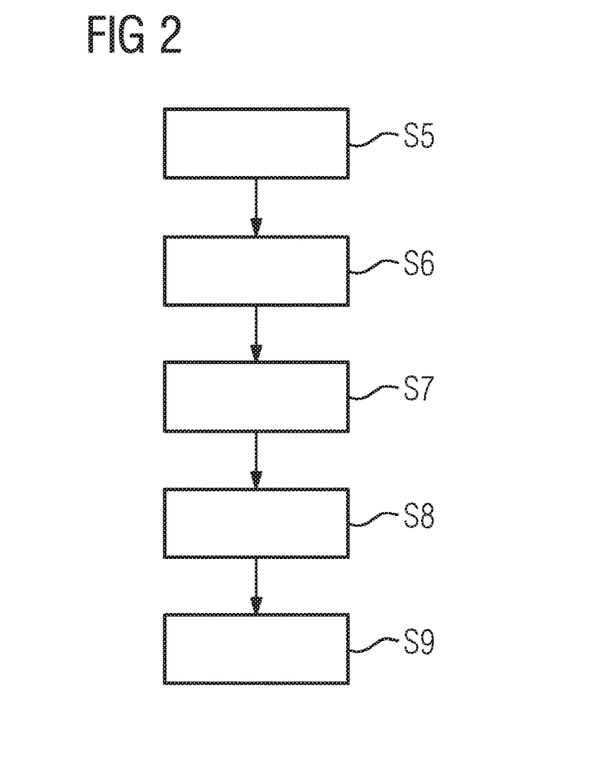
FIG. 2 is a flow chart of a first concrete embodiment.
Figure 3:
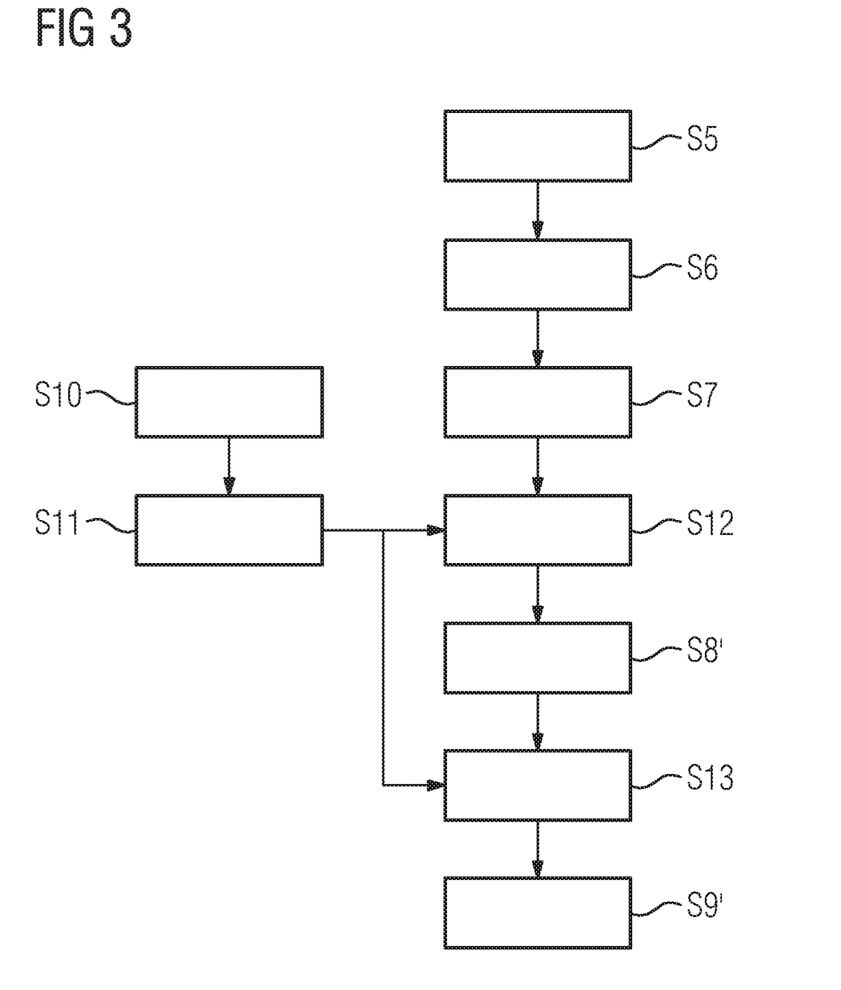
FIG. 3 is a flow chart of a second concrete embodiment.

FIG. 2 and FIG. 3 illustrate two concrete embodiments of the reconstruction pipeline and metal artifact reduction.

In the embodiment of FIG. 2, conventional interpolation (without normalization) is shown. In a step S5, using, for example, filtered back projection (FBP), an initial 3D reconstruction or 3D initial image is determined from the projection image data of acquired projection images which are associated with the highest energy range, in this case, for example, the subset 3 (which may also be termed "highest energy range data"). Due to beam hardening, this 3D initial image contains substantially less metal artifacts.

In a step S6, metal areas are segmented in the 3D initial image, for example by simple thresholding, which is enabled by the sparsity or even absence of artifacts. If the imaged volume also contained iodine or other materials having an attenuation value comparable to the attenuation value of metal, the energy-resolved CT image data 1, in particular the subsets 2, 3, may also be used for a material decomposition step allowing to distinguish between these materials, such that a metal-only mask results.

In a step S7, the metal areas are forward projected using the projection geometries of the projection images to yield metal areas in the projection domain, such that, in a step S8, the projection image data in these metal areas may be removed and an interpolated new data may be added, such that corrected projection images result. In a step S9, the 3D image data set is reconstructed using the corrected projection images.

FIG. 3 shows an embodiment using normalized metal artifact reduction as the metal artifact reducation process, which may also be called "normalized sinogram interpolation". Regarding the general concept, please refer to the article initially cited.

Here, steps S5, S6, and S7 are as described with respect to FIG. 2 and yield metal areas in the projection domain, however, before the interpolation (step S8) takes place, a prior image is determined in step S10 from the 3D initial image or another 3D initial image (which is preferably, in this case, reconstructed using the projection image data of all subsets 2, 3) by multi-thresholding, in this case distinguishing bone from water-equivalent tissue. Material decomposition evaluating the subsets 2, 3 may, again, be used to distinguish bone from iodine or other materials having a comparable attenuation. Would, for example, contrast agent like iodine be classified as bone, the final correction results are likely to have inferior image quality. Using the multi-energy technique, here applying energy thresholds to the photon counting detector, allows spectral analysis to exclude iodine or other contrast agents from determining the prior image in step S10. In particular, a classification mask may be calculated using multiple-material decomposition, assigning, for example, "iodine" or "bone" to respective voxels of the 3D initial image.

In a step S11, the prior image is also forward projected using the projection geometries of the projection images to yield 2D normalization images. These are then used in a step S12 to normalize the projection images by pixel-wise division of the original projection images by the respective normalization images.

The interpolation in the metal areas of the projection domain determined in step S7 takes place in a step S8' using the normalized 2D images, as described in the above-cited article by E. Meyer et al. After interpolation, in a step S13, the corrected normalized 2D images are denormalized using the 2D normalization images determined in step S11, in this case using multiplication. The result are corrected projection images, which can, in a step S9', again be used to reconstruct the artifact-reduced 3D image data set.

Figure 4:
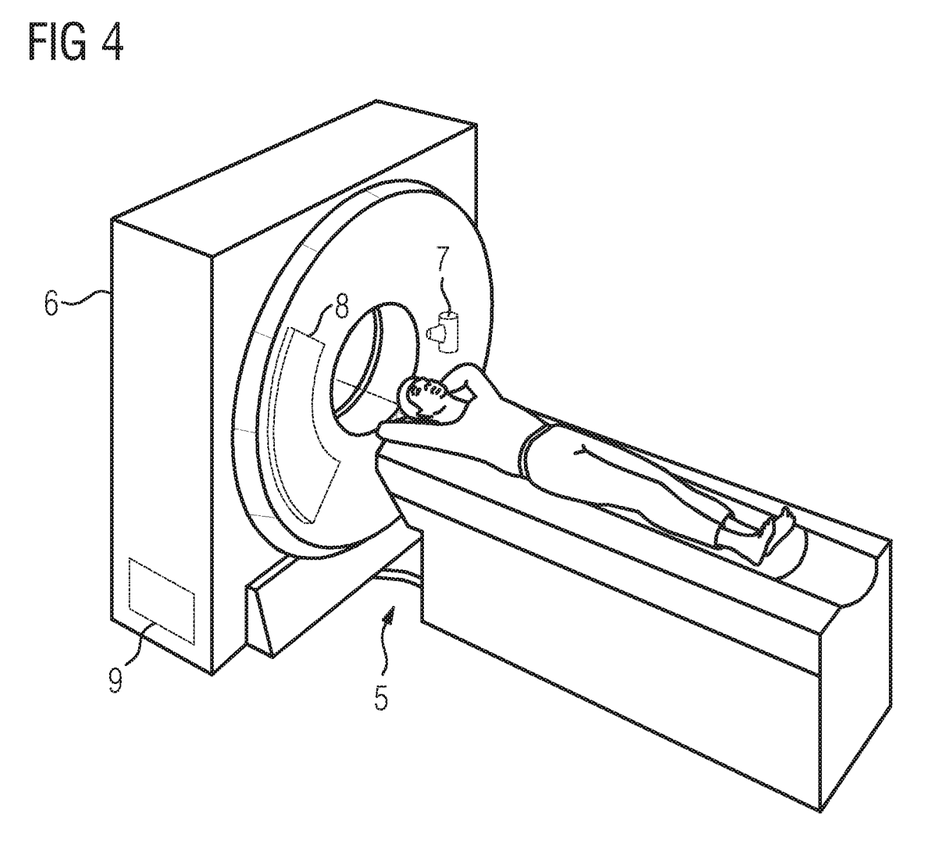
FIG. 4 is a principle drawing of an embodiment of a medical imaging system.

In FIG. 4, a principle drawing of a medical imaging system, in this case a computed tomography system 5, is shown. The computed tomography apparatus comprises a gantry 6, in which an x-ray source 7 and an x-ray detector 8 are movably mounted. The x-ray detector 8 is a photon counting detector. The computed tomography system further comprises, as a control device, a computer 9 which is configured to perform a method according to the invention, in particular as described above with respect to FIGS. 1 to 3.

It is noted that, in another embodiment of a system for metal artifact reduction according to the invention, the computer may also be provided externally to the computed tomography system 5, for example as part of a network communicating with the medical imaging system.

Figure 5:
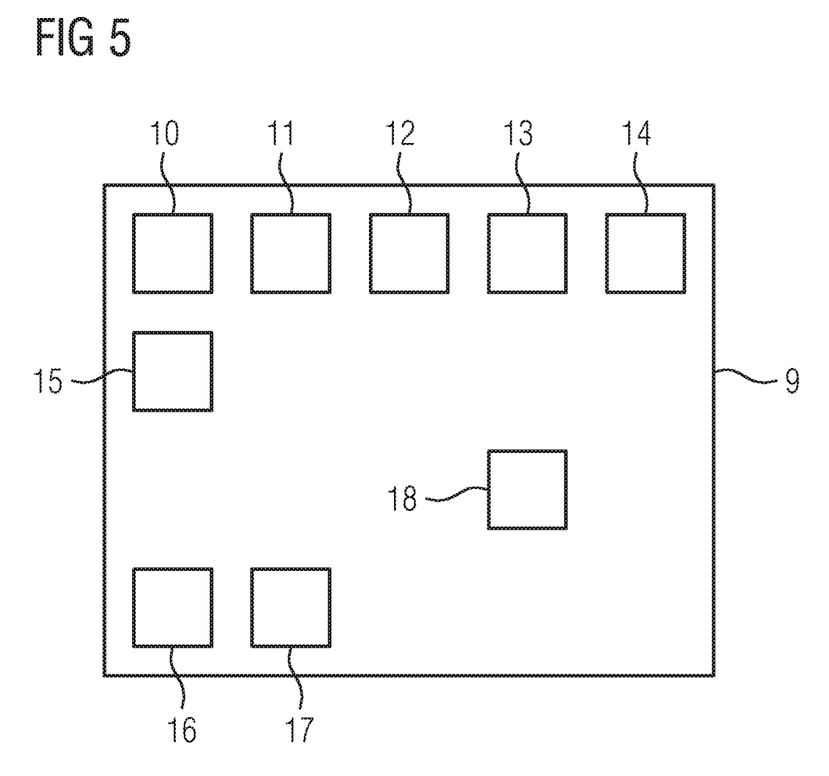
FIG. 5 shows the functional structure of a computer of a system according to an embodiment of the invention.

FIG. 5 shows an example functional structure of a computer of a system according to the invention, in this case of the computer 9.

The computer 9 comprises, as known in the state of the art, a reconstruction unit 10 for performing three-dimensional reconstruction as in steps S5 and S9, S9', a metal segmentation unit 11 for performing the step S6, a forward projection unit 12 for forward projection as in steps S7 and S11, an interpolation unit 13 used in steps S8, S8', optionally a prior image determining unit 14 and a normalization unit 15 for steps S10, S12 and S13, respectively, and an acquisition unit 16 controlling the acquisition of x-ray data with the computed tomography system 5, in particular of the energy-resolved CT image data in step S1. In an adjusting unit 17, suitable energy thresholds may be chosen according to step S2.

The computer 9 further comprises a supplementary unit 18, adapted for applying results of the multi-energy technique, as described, to steps S6 and/or S10, and optionally other steps. In this case, the supplementary unit 18 may be or comprise a material decomposition unit. Additionally or alternatively, the supplementary unit may restrict reconstruction by the reconstruction unit 10 to the highest energy range data in steps S5 and/or prior to step S10.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
   acquiring, using a multi-energy CT technique, energy-resolved CT image data of a volume of an imaged object, wherein the energy-resolved CT image data is associated with multiple energy ranges and includes multiple 2D projection images acquired using a plurality of projection geometries; and
   segmenting metal areas of the multiple 2D projection images in at least one of a projection domain or an image domain;
   correcting the multiple 2D projection images by replacing projection image data with interpolated data in the metal areas, after segmenting; and
   reconstructing a 3D image data set from the multiple 2D projection images, after the correcting; wherein
     interpolation to generate the interpolated data is performed in the projection domain,
     before the interpolation, the multiple 2D projection images are normalized based on a forward projection of a 3D prior image determined from a 3D initial image that is reconstructed from non-normalized multiple 2D projection images, by multi-threshold segmentation, wherein the multiple 2D projection images are denormalized after interpolation, and
     portions of the energy-resolved CT image data are associated with a respective one of the multiple energy ranges and the 3D initial image is reconstructed from a portion of the energy resolved CT image data associated with a highest energy range of the multiple energy ranges.

2. The method of claim 1, wherein
   the segmenting is performed in the image domain by thresholding, and
   the metal areas in the multiple 2D projection images are determined by forward projection.

3. The method of claim 2, wherein the portion of the energy resolved CT image data associated with the highest energy range of the multiple energy ranges is used for the segmenting of the metal areas.

4. The method of claim 1, wherein
   the portion of the energy resolved CT image data associated with the highest energy range of the multiple energy ranges; is used for the segmenting of the metal areas.

5. The method of claim 1, wherein
   spectral information determined as a result of the multi-energy CT technique is used for refining at least one of the multi-threshold segmentation or material classification when determining the 3D prior image.

6. The method of claim 5, wherein the spectral information is used to distinguish between at least one of metal and iodine or bone and iodine to refine the at least one of the multi-threshold segmentation or material classification when determining the 3D prior image.

7. The method of claim 5, wherein the energy resolved CT image data is acquired in a single scan by using a photon counting detector using at least one energy threshold, and wherein the at least one energy threshold is chosen depending on at least one use of the result of the multi-energy CT technique and depending on at least one imaging task information.

8. The method of claim 1, wherein spectral information, determined as a result of the multi-energy CT technique, is used for at least one of the multi-threshold segmentation or material classification.

9. The method of claim 8, wherein the spectral information, determined as a result of the multi-energy CT technique, is used for definition of material specific thresholding masks.

10. The method of claim 1, wherein the energy resolved CT image data is acquired in a single scan by using a photon counting detector using at least one energy threshold.

11. The method of claim 1, wherein the imaged object is a patient.

12. The method of claim 1, wherein the portion of the energy resolved CT image data is associated with the highest energy range of the multiple energy ranges determined using a highest threshold in a photon counting detector.

13. A system comprising:
at least one processor or a computer, to evaluate image data, the at least processor or computer being configured to
acquire, using a multi-energy CT technique, energy-resolved CT image data of a volume of an imaged object, wherein the energy-resolved CT image data is associated with multiple energy ranges and includes multiple 2D projection images acquired using a plurality of projection geometries,
segment metal areas of the multiple 2D projection images in at least one of a projection domain or an image domain,
correct the multiple 2D projection images by replacing projection image data with interpolated data in the metal areas, after segmenting, and
reconstruct a 3D image data set from the multiple 2D projection images, after the correcting, wherein
interpolation to generate the interpolated data is performed in the projection domain,
before the interpolation, the multiple 2D projection images are normalized based on a forward projection of a 3D prior image determined from a 3D initial image that is reconstructed from non-normalized multiple 2D projection images, by multi-threshold segmentation, wherein the multiple 2D projection images are denormalized after interpolation, and
portions of the energy-resolved CT image data are associated with a respective one of the multiple energy ranges and the 3D initial image is reconstructed from a portion of the energy resolved CT image data associated with a highest energy range of the multiple energy ranges.

14. The system of claim 13, wherein the system comprises a medical imaging system.

15. The system of claim 14, wherein the at least one processor or the computer are part of a network, configured to communicate with the medical imaging system.

16. The system of claim 13, wherein the system is a computed tomography system.

17. A non-transitory electronically readable storage medium storing a computer program, the computer program including program elements that, when executed by a computer, cause the computer to perform a method comprising:
acquiring, using a multi-energy CT technique, energy-resolved CT image data of a volume of an imaged object, wherein the energy-resolved CT image data is associated with multiple energy ranges and includes multiple 2D projection images acquired using a plurality of projection geometries;
segmenting metal areas of the multiple 2D projection images in at least one of a projection domain or an image domain;
correcting the multiple 2D projection images by replacing projection image data with interpolated data in the metal areas, after segmenting; and
reconstructing a 3D image data set from the multiple 2D projection images, after the correcting, wherein
interpolation to generate the interpolated data is performed in the projection domain,
before the interpolation, the multiple 2D projection images are normalized based on a forward projection of a 3D prior image determined from a 3D initial image that is reconstructed from non-normalized multiple 2D projection images, by multi-threshold segmentation, wherein the multiple 2D projection images are denormalized after interpolation, and
portions of the energy-resolved CT image data are associated with a respective one of the multiple energy ranges and the 3D initial image is reconstructed from a portion of the energy resolved CT image data associated with a highest energy range of the multiple energy ranges.

* * * * *